(12) United States Patent
Curley

(10) Patent No.: US 11,071,846 B2
(45) Date of Patent: Jul. 27, 2021

(54) DEFLECTION CATHETER FOR AIDING IN BENDING OF A CATHETER

(71) Applicant: Medtronic Vascular, Inc., Santa Rosa, CA (US)

(72) Inventor: Donna Curley, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 188 days.

(21) Appl. No.: 16/130,080

(22) Filed: Sep. 13, 2018

(65) Prior Publication Data

US 2019/0091443 A1 Mar. 28, 2019

Related U.S. Application Data

(60) Provisional application No. 62/558,378, filed on Sep. 14, 2017.

(51) Int. Cl.
*A61M 25/00* (2006.01)
*A61B 17/00* (2006.01)
(Continued)

(52) U.S. Cl.
CPC ... *A61M 25/0071* (2013.01); *A61B 17/00234* (2013.01); *A61M 25/007* (2013.01);
(Continued)

(58) Field of Classification Search
CPC ... A61B 1/00098; A61B 1/00147; A61B 1/01; A61B 2017/00292; A61B 2017/00296; A61B 2017/003; A61B 2017/00318–00323; A61B 2017/00327; A61B 2017/22094–22095; A61B 17/32056; A61B 2017/00358;
(Continued)

(56) References Cited

U.S. PATENT DOCUMENTS 7,621,948 B2 11/2009 Herrmann et al.
8,105,375 B2 1/2012 Navia et al.
(Continued)

OTHER PUBLICATIONS

International Search Report, Application No. PCT/2018/051126, dated Dec. 19, 2018.

*Primary Examiner* — Elizabeth Houston
*Assistant Examiner* — Lindsey Bachman

(57) ABSTRACT

A deflection catheter is disclosed for aiding in bending of a catheter or other elongate medical device transseptally delivered within a left atrium of a heart. The deflection catheter includes a deflection aid assembly having an outer component, an inner component and a connecting band. The connecting band connects a first inner branch segment and a second inner branch segment of the inner component, and also extends between a first outer branch segment and a second outer branch segment of the outer component whereby a catheter receiving opening is defined between the connecting band and the first and second outer branch segments. Proximal/distal movement of the inner component relative to the outer component increases/decreases an area of the catheter receiving opening in order to secure the catheter or other elongate medical device to the deflection aid assembly for subsequent bending by proximally tugging or pulling on the deflection aid assembly.

19 Claims, 18 Drawing Sheets

(51) Int. Cl.
*A61M 25/04* (2006.01)
*A61M 25/06* (2006.01)
*A61B 90/00* (2016.01)
*A61M 25/01* (2006.01)
*A61B 18/00* (2006.01)

(52) U.S. Cl.
CPC ........ *A61M 25/0045* (2013.01); *A61M 25/04* (2013.01); *A61M 25/0662* (2013.01); *A61B 2017/00004* (2013.01); *A61B 2017/00243* (2013.01); *A61B 2017/00358* (2013.01); *A61B 2017/00473* (2013.01); *A61B 2017/00783* (2013.01); *A61B 2017/00853* (2013.01); *A61B 2018/00291* (2013.01); *A61B 2090/037* (2016.02); *A61M 25/0113* (2013.01); *A61M 2025/0046* (2013.01); *A61M 2205/0266* (2013.01); *A61M 2210/125* (2013.01)

(58) Field of Classification Search
CPC ...... A61B 2018/1407; A61B 2018/141; A61B 2018/142; A61B 2018/1422; A61B 2018/144; A61M 25/01; A61M 25/013; A61M 25/0133; A61M 25/0147; A61M 25/0662; A61M 2025/015; A61M 2025/0163; A61M 2025/018; A61M 2025/0197
See application file for complete search history.

(56) References Cited

U.S. PATENT DOCUMENTS

| | | | |
|---|---|---|---|
| 8,591,460 | B2 | 11/2013 | Wilson et al. |
| 9,078,994 | B2 | 7/2015 | Rosenman et al. |
| 2004/0260394 | A1 | 12/2004 | Douk et al. |
| 2011/0087222 | A1* | 4/2011 | Miller ................ A61B 18/14 606/46 |
| 2011/0208297 | A1 | 8/2011 | Tuval et al. |
| 2012/0059458 | A1 | 3/2012 | Buchbinder et al. |
| 2013/0060328 | A1 | 3/2013 | Rothstein |
| 2013/0226290 | A1 | 8/2013 | Yellin et al. |
| 2013/0231735 | A1 | 9/2013 | Deem et al. |
| 2013/0310928 | A1 | 11/2013 | Morriss et al. |
| 2013/0338667 | A1* | 12/2013 | Daignault ......... A61B 18/1485 606/47 |
| 2014/0039611 | A1 | 2/2014 | Lane et al. |
| 2014/0276908 | A1 | 9/2014 | Raybin et al. |
| 2014/0350669 | A1 | 11/2014 | Gillespie et al. |
| 2014/0379074 | A1 | 12/2014 | Spence et al. |
| 2015/0066047 | A1 | 3/2015 | Chu et al. |
| 2015/0119981 | A1 | 4/2015 | Khairkhahan et al. |
| 2015/0297346 | A1 | 4/2015 | Duffy et al. |
| 2015/0148814 | A1 | 5/2015 | Chu |
| 2015/0238315 | A1 | 8/2015 | Rabito et al. |
| 2015/0265334 | A1* | 9/2015 | Franke ................. A61B 18/14 606/34 |

* cited by examiner

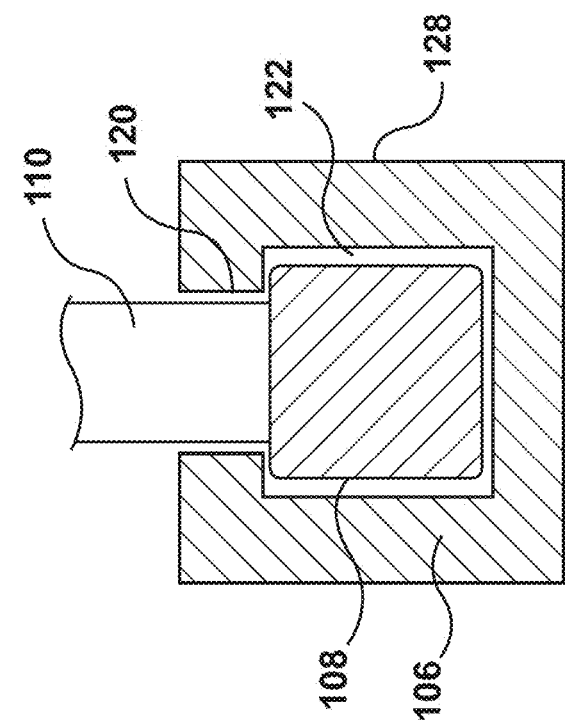
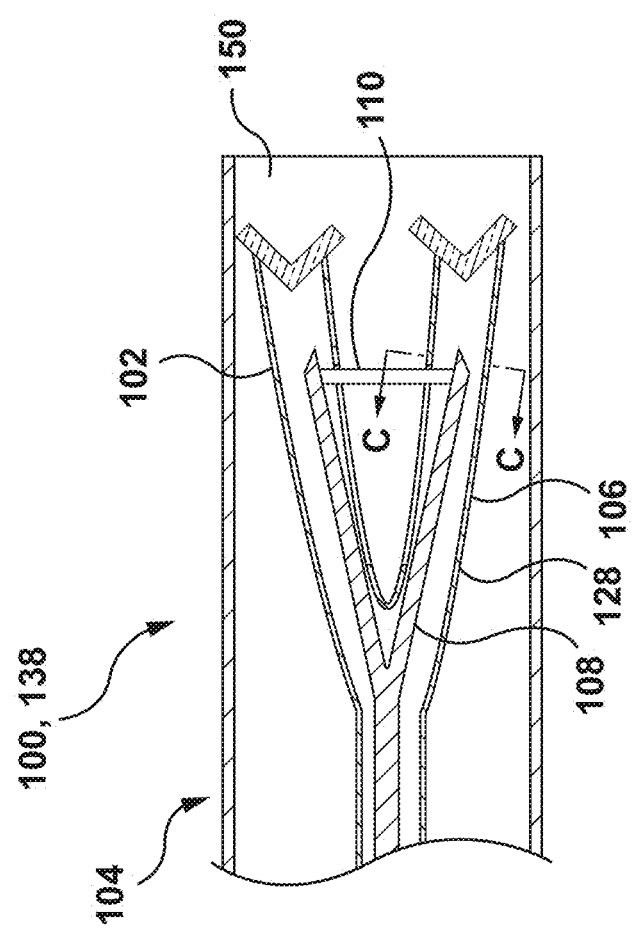

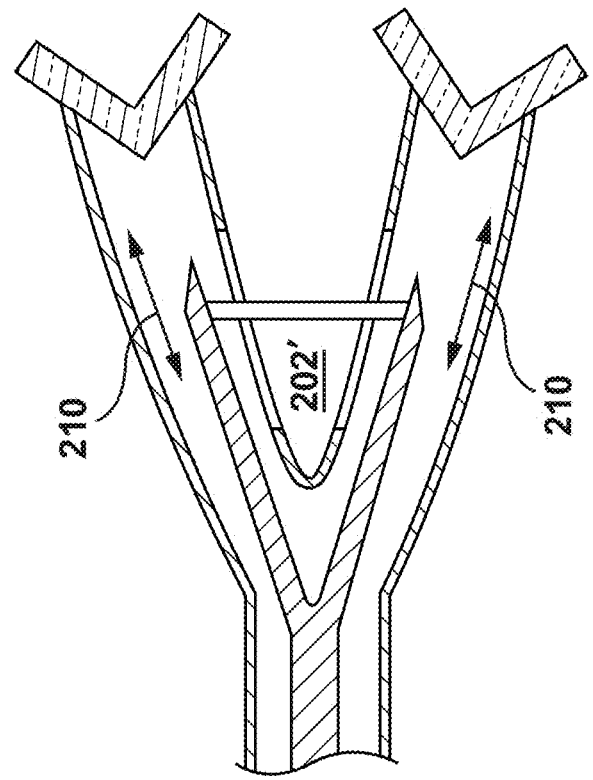
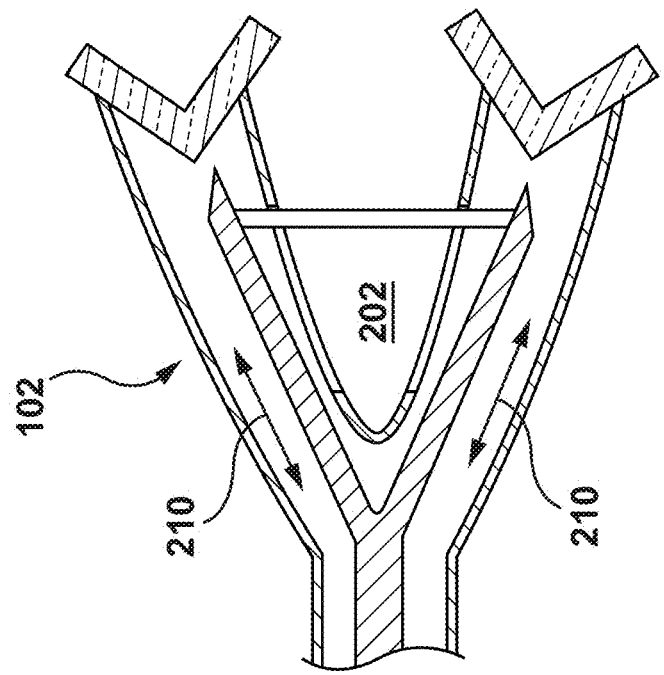
FIG. 2A
FIG. 2B

DEFLECTION CATHETER FOR AIDING IN BENDING OF A CATHETER

CROSS-REFERENCE TO RELATED APPLICATIONS

This application claims the benefit under 35 U.S.C. § 119(e) of U.S. Provisional Application No. 62/558,378 filed Sep. 14, 2017, the contents of which are incorporated by reference herein in their entirety.

FIELD OF THE INVENTION

The invention relates to deflection catheters for use within a left atrium, as well as deflection catheter systems and methods of use thereof. In particular, the deflection catheters aid in bending and alignment of delivery catheters within the left atrium during transseptal delivery of prostheses held therein.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses and other medical device, such as annuloplasty clips and mechanism, have been developed for repair and replacement of diseased and/or damaged heart valves. Such heart valve prostheses and medical devices can be percutaneously delivered and deployed at the site of the diseased heart valve through catheter-based delivery systems. Such heart valve prostheses and medical devices can be delivered while in a low-profile or compressed/contracted configuration so that they may be advanced through the patient's vasculature. Once positioned at the treatment site, the heart valve prosthesis, or other medical device, may be deployed to engage tissue at the diseased heart valve region to, for instance, anchor the heart valve prosthesis in position or effect repair. While minimally invasive methods for heart valve repair and/or replacement exist, challenges remain when providing catheter-based therapies via a transseptal approach within a left atrium. For example, catheter delivery approaches and techniques for mitral valve replacement may utilize a transseptal approach. However, with a heart valve prosthesis retained within a distal segment of a catheter-based delivery system, challenges such as turning or bending the distal segment of the delivery system within the confined space of the left atrium may make positioning of a heart valve prosthesis in the native mitral valve very difficult, if not impossible. Similarly, catheter delivery approaches and techniques for aortic valve replacement may utilize percutaneous approach within the aorta, including over the aortic arch. In such an approach, the catheter-based delivery system tends to track on the outer curvature of the aorta. Tracking on the outer curvature of the aorta results in difficulty in crossing the native leaflets of the aortic valve.

What is needed is a device to aid in the bending or deflection of delivery catheters when used in left atrial procedures, aortic valve procedures, or other procedures in which it would be beneficial to bend the delivery catheter. Embodiments hereof are directed to a deflection catheter that addresses the challenges described above.

BRIEF SUMMARY OF THE INVENTION

Embodiments hereof are directed to a deflection catheter for aiding in bending of a catheter. The deflection catheter comprises a deflection aid assembly including an outer component, an inner component and a connecting band. The outer component has a proximal segment, a first outer branch segment, and a second outer branch segment, and the inner component has a proximal segment slideably disposed within the proximal segment of the outer component, and has a first inner branch segment and a second inner branch segment slideably disposed with the first outer branch segment and the second outer branch segment, respectively, of the outer component. The connecting band connects the first inner branch segment and the second inner branch segment of the inner component, and also extends between the first outer branch segment and the second outer branch segment of the outer component to thereby define a catheter receiving opening between the connecting band and the first outer branch segment and the second outer branch segment. In an embodiment, each of the first outer branch segment and the second outer branch segment of the outer component has a slotted opening through which the connecting band passes so as to connect the first inner branch segment and the second inner branch segment disposed, respectively, therein. Proximal and distal movement of the inner component relative to the outer component increases or decreases an area of the catheter receiving opening. In embodiments hereof, an attachment mechanism may be associated with at least one of the first outer branch segment or the second outer branch segment of the outer component.

In an embodiment, the deflection catheter further includes an elongate tubular sheath defining a lumen within which the deflection aid assembly is slideably disposed. In a delivery configuration, when the deflection aid assembly is contained entirely within the lumen of the elongate tubular sheath, the first outer branch segment and the second outer branch segment of the outer component, with the first inner branch segment and the second inner branch segment of the inner component disposed respectively therein, are held in a low-profile state. In a deployed configuration, when the deflection aid assembly is translated to be free of a distal end of the elongate tubular sheath, the first outer branch segment and the second outer branch segment, with the first inner branch segment and the second inner branch segment of the inner component disposed respectively therein, diverge from each other to a deployed state. In an embodiment, upon deployment of the deflection aid assembly from the distal end of the elongate tubular sheath, the proximal segments of the inner and outer components assume a curved configuration.

Embodiments hereof are also directed to methods of bending a catheter or other elongate medical device. The method comprises advancing a deflection catheter in accordance herewith to a desired location within the vasculature or a heart, and deploying the deflection aid assembly from a distal end of an elongate tubular sheath of the deflection catheter whereby the first outer branch segment and the second outer branch segment of the outer component, with the first inner branch segment and the second inner branch segment of the inner component disposed respectively therein, diverge from each other. Thereafter, the method may include attaching attachment mechanism(s) of the deflection aid assembly to a wall at the desired location. The method comprises advancing a catheter or other elongate medical device to the desire location, and advancing at least a distal tip of the catheter or other elongate medical device through a catheter receiving opening of the deflection aid assembly of the deflection catheter. The method comprises proximally sliding the inner component of the deflection aid assembly relative to the outer component of the deflection aid assembly so as to decrease the area of the catheter receiving opening and thereby to secure the catheter or other elongate medical device between the connecting band and the first outer branch segment and the second outer branch segment of the outer component, and thereafter bending the catheter or other elongate medical device by proximally tugging or pulling on the deflection aid assembly of the deflection catheter.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1B shows a sectional view of the distal portion of the deflection catheter of FIG. 1 with the deflection aid assembly in a restrained, delivery configuration in accordance with embodiments hereof.

FIG. 1C shows a cross-sectional view of the deflection aid assembly of FIG. 1B taken through line C-C in accordance with embodiments hereof.

FIG. 2A shows a sectional view of a distal portion of a deflection aid assembly illustrating a catheter receiving opening in accordance with embodiments hereof.

FIG. 2B shows a sectional view of a distal portion of a deflection aid assembly illustrating a constricted catheter receiving opening in accordance with embodiments hereof.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician.

The following detailed description is merely exemplary in nature and is not intended to limit the invention or the application and uses of the invention. Although the description of embodiments hereof is in the context of procedures within the left atrium, the system described herein can also be used in other areas of the heart or body. Furthermore, there is no intention to be bound by any expressed or implied theory presented in the preceding technical field, background, brief summary or the following detailed description.

In embodiments, provided herein is a deflection catheter for use in left atrial procedures. As noted above, directing or positioning a catheter or other instrument in the left atrium and also within the mitral valve can be difficult due to the tight angles and bends that the catheter needs to make. With the deflection catheter described herein, a catheter, such as a delivery catheter, can be easily manipulated and bent to the required configuration for left atrial procedures.

Figure 1:
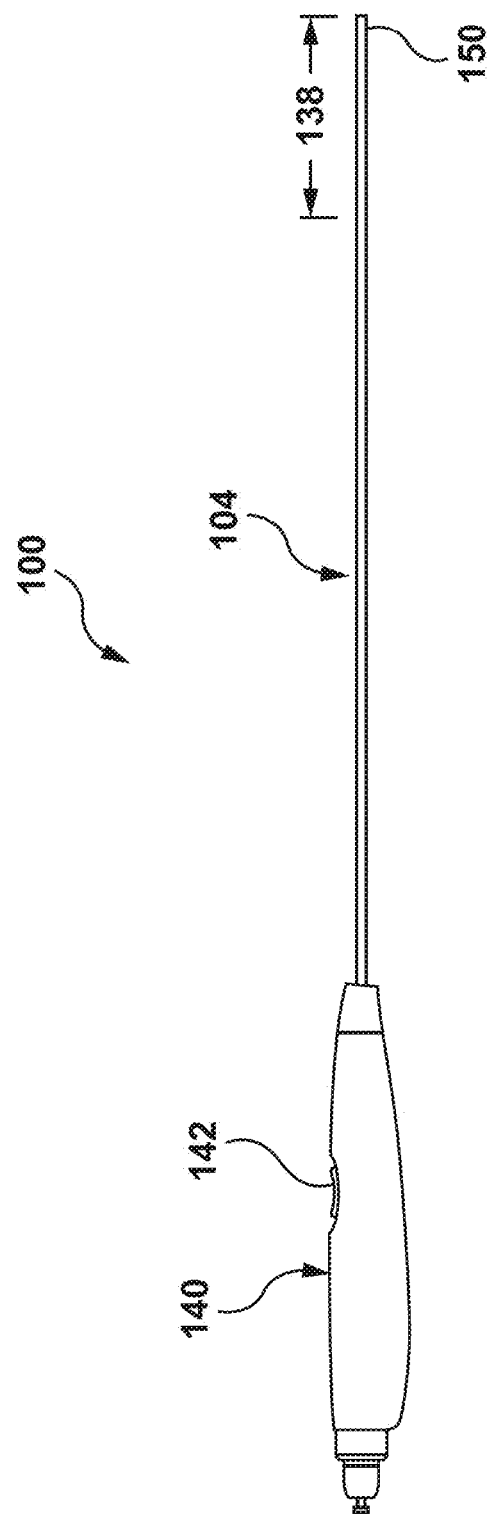
FIG. 1 is a side view of a deflection catheter in accordance with embodiments hereof.
Figure 1A:
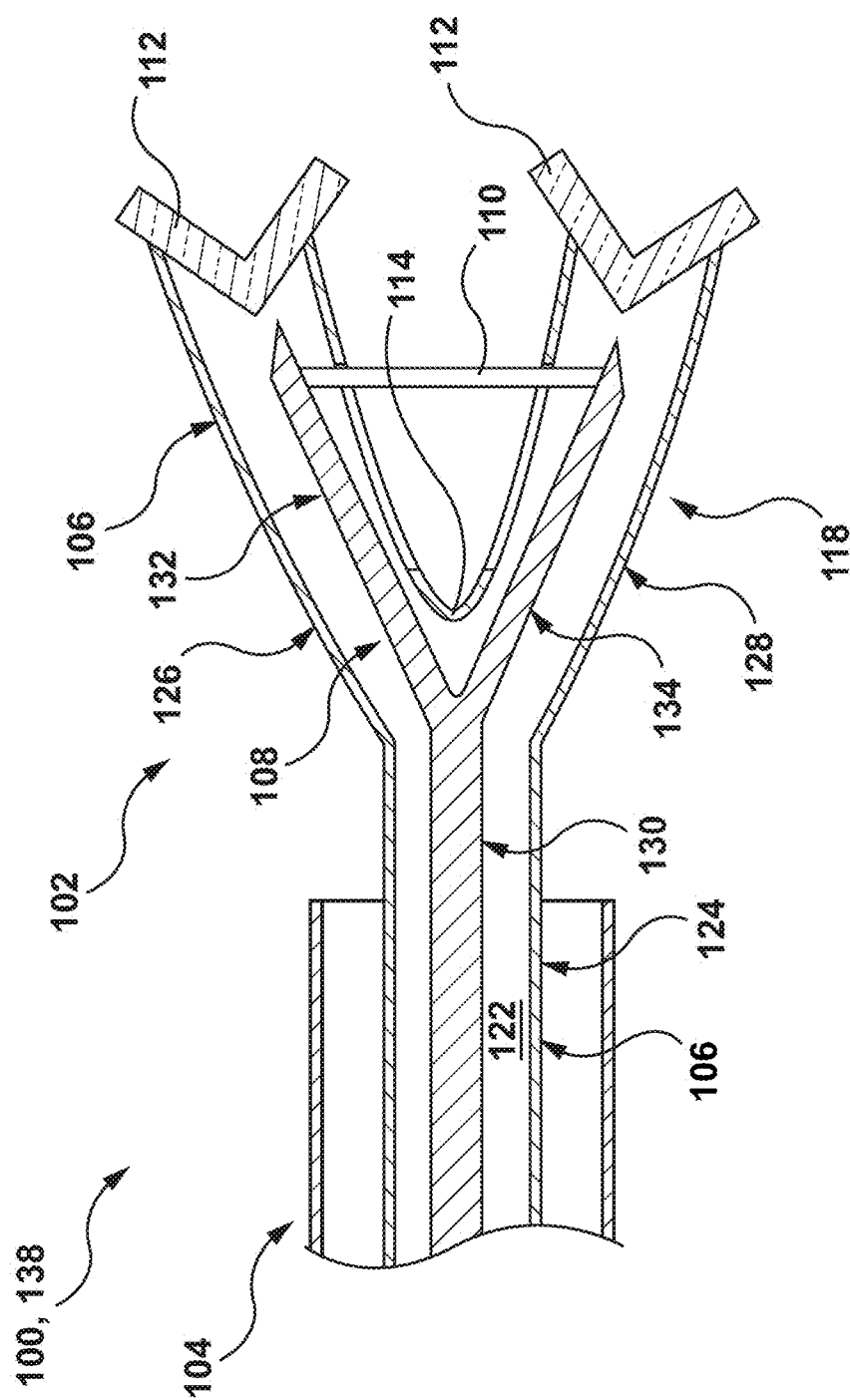
FIG. 1A shows a sectional view of a distal portion of the deflection catheter of FIG. 1 with a deflection aid assembly in a deployed configuration in accordance with embodiments hereof.

FIG. 1 is a side view of a deflection catheter 100 in accordance with embodiments hereof having a handle component 140 at a proximal end thereof and an elongate tubular sheath 104, which with further reference to FIG. 1A, includes a deflection aid assembly 102 slideably disposed with the elongate tubular sheath 104. FIG. 1A is a sectional view of a distal portion 138 of the deflection catheter 100 with the deflection aid assembly 102 in a deployed configuration in accordance with embodiments hereof. The deflection aid assembly 102 includes an outer component 106 having a proximal segment 124, a first outer branch segment 126 and a second outer branch segment 128, the first and second outer branch segments 126, 128 being forked relative to the proximal segment 124 as shown in FIG. 1A. In this manner, the first and second outer branch segments 126, 128 distally extend from the proximal segment 124 to form a generally Y-shape of the outer component 106. In an embodiment, the proximal segment 124 of the outer component 106 suitably extends to the handle component 140 of the deflection catheter 100.

An inner component 108 is slideably disposed within a lumen 122 of the outer component 106. The inner component 108 includes a proximal segment 130, a first inner branch segment 132 and a second inner branch segment 134, the first and second inner branch segments 132, 134 being forked relative to the proximal segment 130 as shown in FIG. 1A. In this manner, the first and second inner branch segments 132, 134 distally extend from the proximal segment 130 to form a generally Y-shape of the inner component 108. In an embodiment, the first inner branch segment 132 and the second inner branch segment 134 distally extend from the proximal segment 130 of the inner component 108 such that the inner component 108 has a generally Y-shape that is substantially similar to the generally Y-shape of the outer component 106. In an embodiment, the proximal segment 130 extends to the handle component 140 of the deflection catheter 100 and is operably connected to an actuation mechanism 142 thereof, as would be understood by one of skill in the art.

The deflection aid assembly 102 also includes a connecting band 110 connecting the first inner branch segment 132 and the second inner branch segment 134 of the inner component 108. The space formed between the connecting band 110, and the first outer branch segment 126 and the second outer branch segment 128 of the outer component 106 creates a catheter receiving opening 202 (see FIG. 2A).

In embodiments, the connecting band 110 is a flexible, resilient element, for example, formed from one or more filaments, fibers, sutures, or bands. Connecting band 110 may comprise, for example, one or more elastomeric materials, polymers, rubbers or silicones, that when brought against the surface of a delivery catheter, will hold or secure the delivery catheter in place, but not cause any unwanted dents, deformations or otherwise harm the structure of the delivery catheter or the elements that the delivery catheter may contain. In other embodiments, however, the connecting band 110 can be a semi-rigid, rigid, semi-stiff, or stiff element, and may have a contour or bend, so as to accommodate receiving the shape of a delivery catheter when moved by the inner component 108 to constrict the catheter receiving opening (202', see FIG. 2B). In some embodiments, connecting band 110 may comprise, for example, one or more hard or semi-hard plastics, and/or metals. In some embodiments, connecting band 110 may comprise, for example, one or more shape memory materials.

The deflection aid assembly 102 further includes an attachment mechanism 112 associated with at least one of the first outer branch segment 126 or the second outer branch segment 128 of the outer component 106. Though in further embodiments, both of the first and second outer branch segments 126, 128 include a respective attachment mechanism 112.

As shown in FIG. 1C, the inner component 108 is slideably disposed within the lumen 122 defined by the outer component 106. As shown in FIG. 1C, the proximal segment 130 of the inner component 108 is slideably disposed within the proximal segment 124 of the outer component 106, and the first inner branch segment 132 and the second inner branch segment 134 of the inner component 108 are slideably disposed with the first outer branch segment 126 and the second outer branch segment 128, respectively, of the outer component 106. Accordingly some space or a gap exists surrounding the inner component 108 within the lumen 122, to allow for the inner component 108 to slide relative to the outer component 106. In other embodiments, however, the inner component 108 can be directly against, or abut with, the sides of the lumen 122, while still allowing for sliding within the outer component 106. Suitably, a lubricant or friction reducer can also be included within the lumen 122 to facilitate the sliding of the inner component 108. As shown in FIGS. 2A-2B, the inner component 108 is configured to increase or decrease the catheter receiving opening 202, for example, to decrease the catheter receiving opening from an area shown by opening 202 in FIG. 2A to an area shown by opening 202' in FIG. 2B via sliding motion 210, wherein an area of the catheter receiving opening may be increased or decreased by proximal or distal movement of the inner component 108 relative to the outer component 106. As described herein, by decreasing the catheter receiving opening 202, a delivery catheter can be held or secured within the catheter receiving opening 202, and ultimately bent or positioned as desired for use in a left atrial procedure.

FIG. 1C also shows a slotted opening 120 in the second outer branch segment 128 of the outer component 106 through which connecting band 110 can pass, and thus allow for connection between the first inner branch segment 132 and the second inner branch segment 134 of the inner component 108, which reside within respective portions of the lumen 122 that are defined within the first and second outer branch segments 126, 128 of the outer component 106. Accordingly, each of the first and second outer branch segments 126, 128 of the outer component 106 includes a respective slotted opening 120, which substantially correspond to, or align with, each other across the catheter receiving opening 202.

In some embodiments, tissue attachment mechanism 112 is detachable from the first outer branch segment 126 and/or the second outer branch segment 128 of the outer component 106. As used herein "attachment mechanism" refers to an element which is connected to the outer component 106 and also contains a portion that can be directly attached to myocardial tissue (wall) of the heart. Exemplary attachment mechanisms include barbs, hooks, screws, adhesive pads or adhesive elements, pointed articles, etc. In some embodiments, attachment mechanism 112 may include one or more breakaway elements or one or more biodegradable elements which connect attachment mechanism 112 to the outer component 106. The ability to detach attachment mechanism 112 from the outer component 106 assists with the deflection aid assembly 102 bending or deflecting a delivery catheter which has been introduced into the catheter receiving opening 202 of the deflection aid assembly 102. If attachment mechanism 112 is separated from the outer component 106 and remains attached to the wall of the heart, the attachment mechanism 112 can be prepared from a biodegradable material, can be later removed from the subject, or can be left in place, if desired.

In some embodiments, the attachment mechanism 112 remains connected or coupled to the first outer branch segment 126 and/or the second outer branch segment 128 of the outer component 106 while the attachment mechanism 112 is detachable from myocardial tissue (wall) of the heart. Methods to make attachment mechanism 112 detachable from myocardial tissue of the heart include, but not limited to, barbs that can be retracted or broken off, screws which can be turned and removed, suction members including one or more suction pads, pods, and/or ports, which can be turned on and off, rapidly degradable polymers or adhesives which have reduced adhesive properties within minutes of attachment to the inner tissue surface of the heart to facilitate detachment, etc. The ability to detach attachment mechanism 112 from myocardial tissue assists with the deflection aid assembly 102 bending or deflecting a delivery catheter, which has been introduced into the catheter receiving opening 202 of the deflection aid assembly 102.

To aid in insertion, as well as movement, of a delivery catheter in the catheter receiving area 220 of the deflection aid assembly 102, an inner surface 114 of the outer component 106 can also include a low friction coating, adjacent the catheter receiving opening 202. Examples of low friction coatings include various polymers, such as fluoropolymers like TEFLON® (polytetrafluoroethylene), fluorinated ethylene propylene, and other materials.

Figure 3:
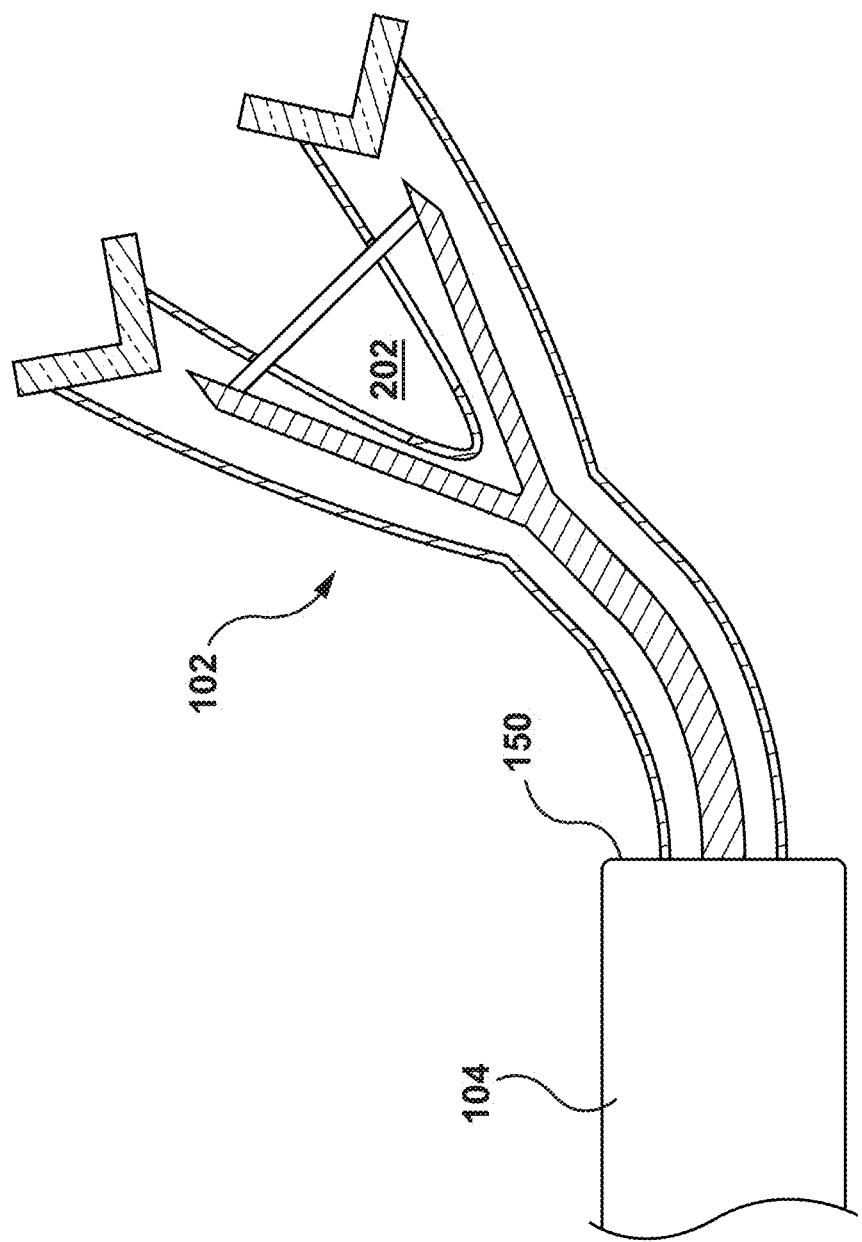
FIG. 3 shows a sectional view of a distal portion of a deflection aid assembly being deployed from an elongate tubular sheath of a deflection catheter in accordance with embodiments hereof.

As shown in FIG. 1B, the deflection aid assembly 102 is contained within the elongate tubular sheath 104. Following introduction into the left atrium of a heart, the deflection aid assembly 102 is deployed from a distal end 150 of the elongate tubular sheath 104. As shown in FIG. 1B, when the deflection aid assembly 102 is contained within the elongate tubular sheath 104, the deflection aid assembly 102, and thus the outer component 106 and the inner component 108, have a compressed low-profile state. In an embodiment, as shown in FIG. 3, upon deployment from the distal end 150 of the elongate tubular sheath 104, the deflection aid assembly 102 may assume a curved configuration. In addition, the outer component 106 and the inner component 108 of the deflection aid assembly 102 may assume a deployed state, when the deflection aid assembly 102 is translated to be free of the distal end 150 of the elongate tubular sheath 104, with the first outer branch segment 126 and the second outer branch segment 128, having the first inner branch segment 132 and the second inner branch segment 134 disposed respectively therein, diverging from each other, such that the inner and outer components 106, 108 assume a generally Y-shape. The generally Y-shape of the deployed deflection aid assembly 102 presents and opens the catheter receiving opening 202 for receiving a delivery catheter there through. The elongate tubular sheath 104 is suitably a tubular element operably coupled to an actuation mechanism (not shown) of the handle component 140.

In embodiments hereof, an elongate tubular shaft or component(s) and/or segment(s) of the outer and inner components 106, 108 and the elongate tubular sheath 104 may be formed of one or more polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. In other embodiments of an elongate tubular shaft or component(s) and/or segment(s) of the outer and inner components 106, 108 and the elongate tubular sheath 104 in accordance herewith, one or more proximal or distal segments thereof may include one or more elastomeric materials, polymers, metals, shape memory materials, radiopaque materials, radiographic materials, imaging materials, wires, rings, bands, etc. In some embodiments of an elongate tubular shaft or component(s) and/or segment(s) of the outer and inner components 106, 108 and the elongate tubular sheath 104 in accordance herewith, a proximal segment thereof may include or be a hypotube of a medical grade metal, for example, stainless steel, with outer and inner tubes of distal segments thereof being formed from any of the materials listed above.

Figure 4:
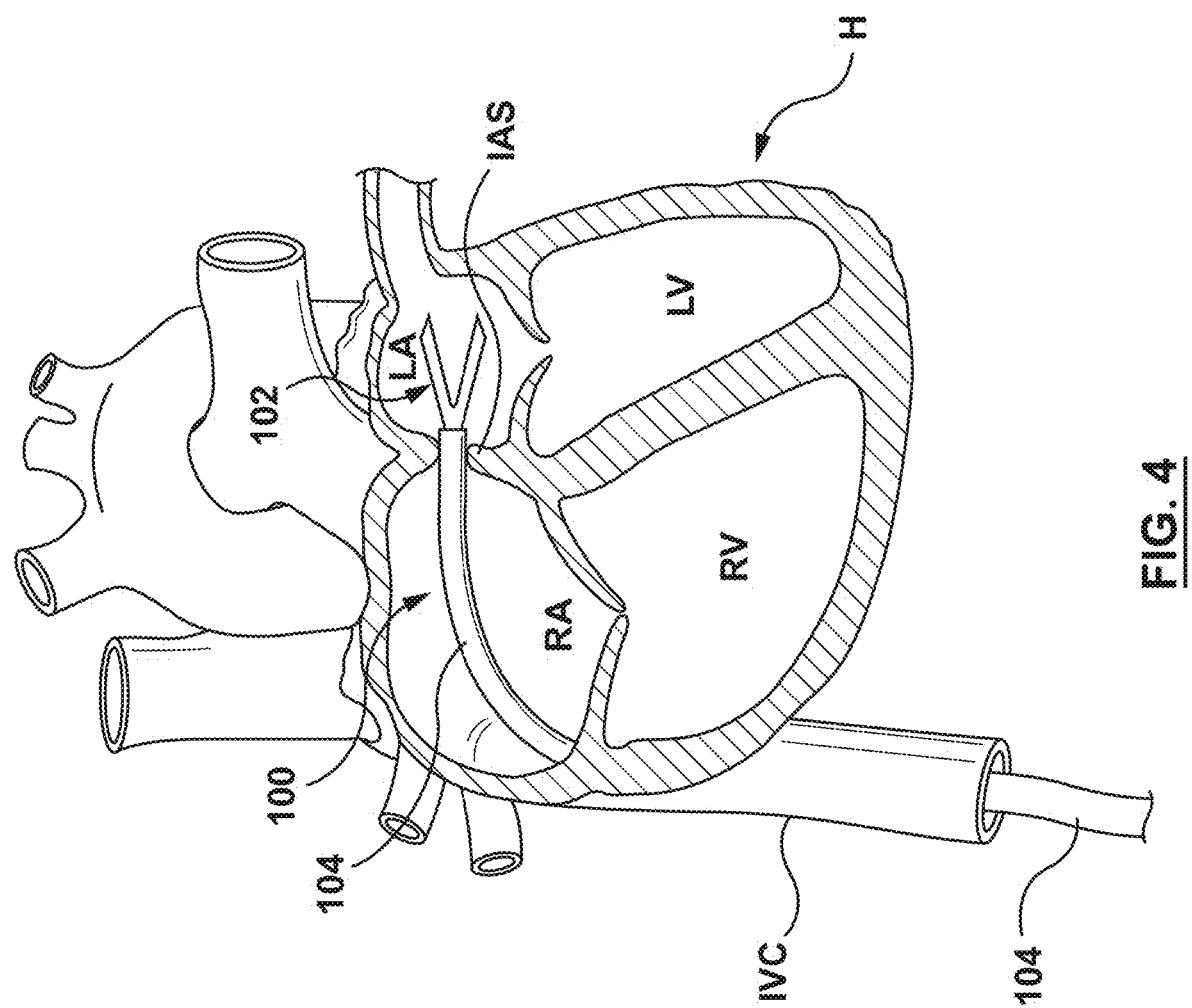
FIG. 4 shows introduction, advancement and positioning of a deflection catheter into a left atrium of a heart and deployment of a deflection aid assembly from an elongate tubular sheath of the deflection catheter in accordance with embodiments hereof.

FIG. 4 shows a schematic representation of the introduction, advancement and positioning of a deflection catheter 100, as described herein, within a heart H. In embodiments, components of the deflection catheter 100, including at least proximal ends of the elongate tubular sheath 104, the proximal segment 124 of the outer component 106 and the proximal segment 130 of the inner component 108, remain external to the subject (patient), and operably coupled to actuation mechanisms of the handle component 140, so as to allow a clinician to deploy and control the various components of the deflection catheter 100. During advancement through the vasculature, the deflection aid assembly 102 is held in a delivery configuration within the elongate tubular sheath 104 of the deflection catheter 100 (see FIG. 1B).

As described herein, the deflection catheters are suitably used for positioning a delivery catheter in a left atrial procedure. With reference to FIG. 4, the deflection catheter 100 is shown after having been introduced into the vasculature via a percutaneous entry point, for example via the Seldinger technique, and tracked through the vasculature into a left atrium LA of a heart H. Prior thereto, intravascular access to the right atrium RA may be achieved via a percutaneous access site to femoral venous access up to the inferior venal cava IVC, or other known access routes. Thereafter, a guidewire (not shown) may be advanced through the circulatory system, eventually arriving at the heart H. The guidewire may be directed into the right atrium RA, may traverse the right atrium and may be made to traverse, with the aid of a transseptal needle or pre-existing hole, the interatrial septum IAS, thereby entering the left atrium LA. Once the guidewire is positioned, the endoluminal entry port and the interatrial septum IAS are dilated to permit entry of a guide catheter (not shown) into the left atrium LA. Thereafter, the deflection catheter 100 may be advanced (optionally over the guidewire and/or through a guide catheter) into the left atrium LA through the punctured interatrial septum IAS and positioned proximate or upstream to the native mitral valve MV. Although described as a transfemoral antegrade approach for percutaneously accessing the mitral valve MV, the deflection catheter 100 may be positioned within the left atrium LA of the heart H via different methods such as a transseptal antegrade approach via a thoracotomy for accessing the mitral valve MV. In addition, although described with the use of a guide catheter and/or a guidewire, in another embodiment hereof the deflection catheter 100 may access the left atrium LA without the use of a guidewire and/or a guide catheter. For example, in methods in accordance herewith, the deflection catheter 100 as described herein is suitably advanced up the femoral vein and the inferior vena cava IVC, until reaching the right atrium RA. Additional methods of introducing the deflection catheter 100 into the heart H are also encompassed herein and are known by those of ordinary skill in the art.

Figure 5:
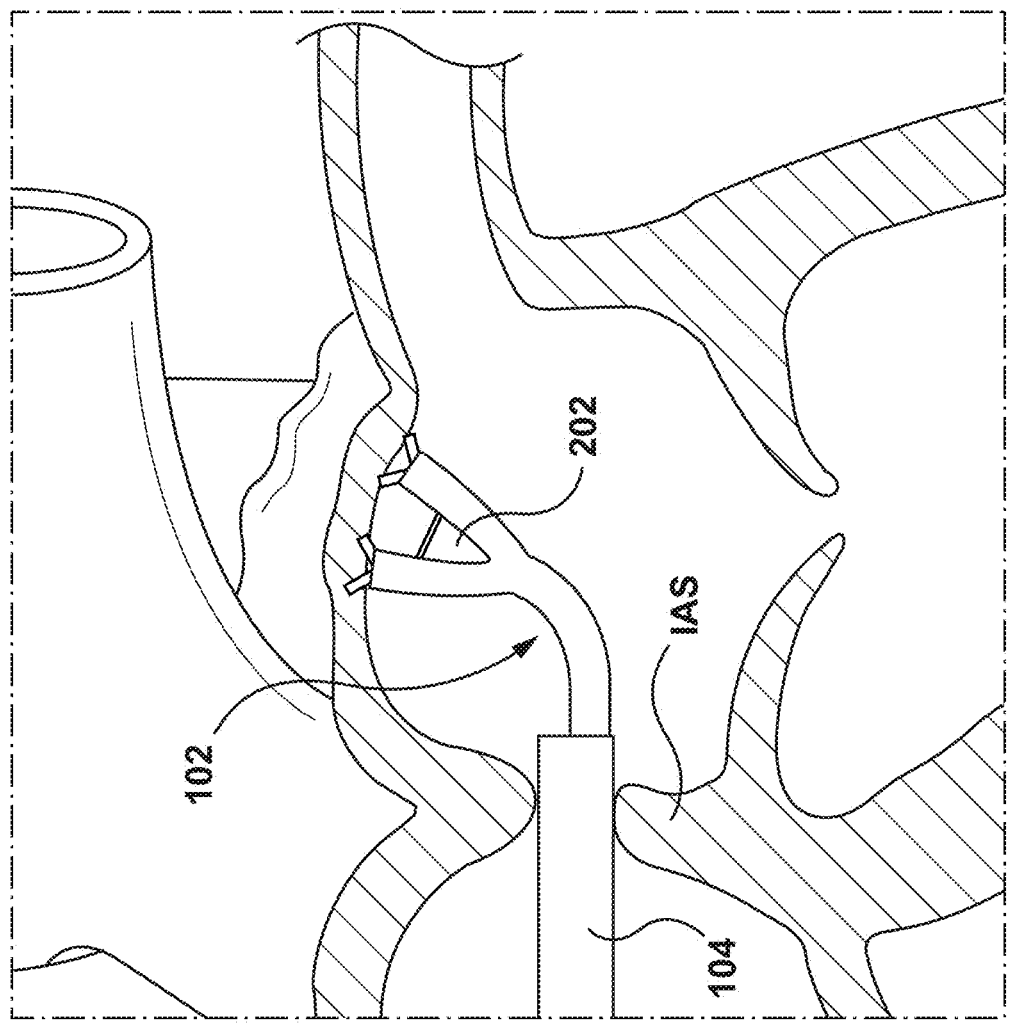
FIG. 5 shows attachment of the deflection aid assembly to a wall of the left atrium in accordance with embodiments hereof.

After the deflection catheter 100 is advanced through interatrial septum IAS, which is the wall of tissue that separates the right and left atria of the heart, and into the left atrium LA of the heart H, the deflection aid assembly 102 is then deployed from the distal end 150 of the elongate tubular sheath 104, as shown in FIG. 4. In the deployed configuration, as shown in FIG. 3, the deflection aid assembly 102 may assume a generally Y-shape, as the first outer branch segment 126 and the second outer branch segment 128 of the outer component 106, with the first inner branch segment 132 and the second inner branch segment 134 of the inner component 108 disposed respectively therein, diverge from each other. As well upon deployment of the deflection aid assembly 102 from the distal end 150 of the elongate tubular sheath 104, the proximal segments 124, 130 of the outer and inner components 106, 108 may assume a curved configuration. When the deflection aid assembly 102 is in the deployed configuration, as shown in FIGS. 2A and 5, the catheter receiving opening 202 is open and accessible, and the curved configuration permits for attaching of attachment mechanisms 112 to myocardial tissue of the heart (H).

Figure 6:
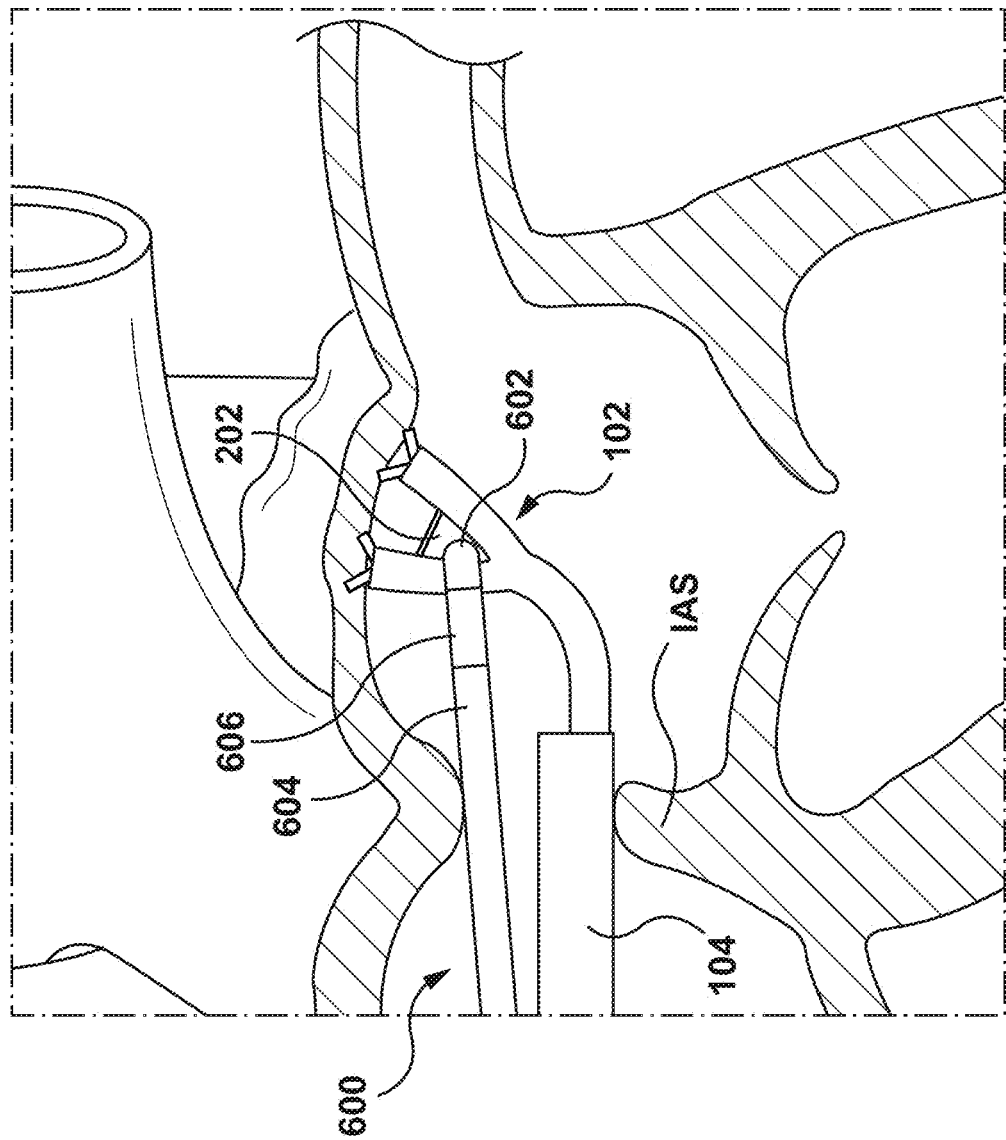
FIG. 6 shows introduction and advancement of a delivery catheter into the left atrium of the heart, and into a catheter receiving opening of the deflection aid assembly in accordance with embodiments hereof.

The methods provided herein further include (see FIG. 6) introducing a delivery catheter 600, through the interatrial septum (IAS), and into the left atrium of the heart. The delivery catheter 600 may include a distal tip 602 (i.e., catheter tip or nosecone) and an elongate tubular sheath 604, which may include a distal segment 606, such as a capsule segment, within which a medical device, such as a prosthetic heart valve (not shown), may be held in a delivery state, as shown in FIG. 6. The delivery catheter 600 may assume different forms, construction and features described, by example and not by way of limitation, in U.S. Pat. No. 8,876,893 to Dwork, U.S. Pat. No. 7,662,186 to Bragga et al., U.S. Pat. No. 7,740,655 to Birdsall, and/or U.S. Pat. No. 8,579,963 to Tabor, each of which is incorporated by reference herein in their entirety. Delivery catheters, also known as medical catheters, are typically adapted to deliver and deploy medical devices, such as prosthetic heart valves, stent-grafts, and stents to selected targeted sites in the body. Delivery catheters may also be utilized with a guidewire. Medical devices typically are releasably carried within a distal region of the delivery catheter in a radially compressed delivery state as the catheter is navigated to and positioned at a target treatment/deployment site.

Figure 7:
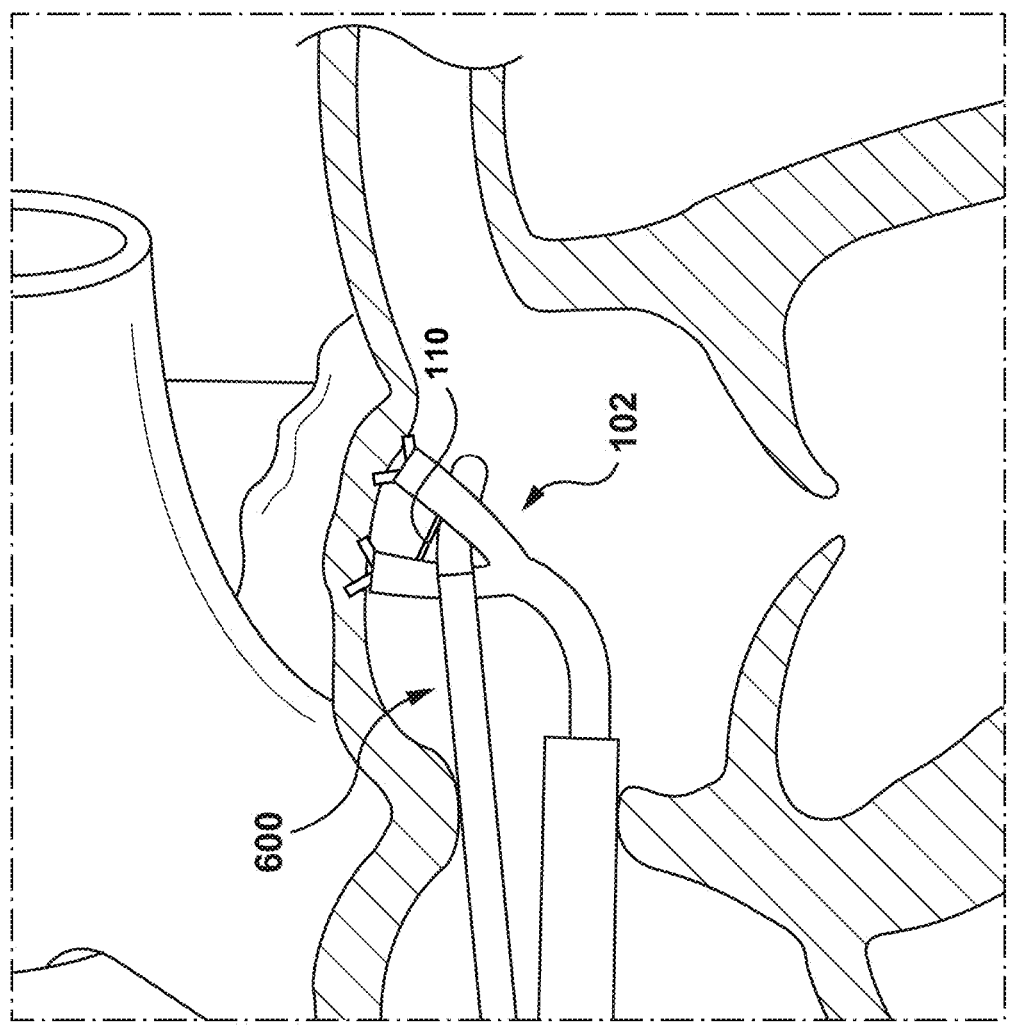
FIG. 7 shows securing of the delivery catheter by the deflection aid assembly in accordance with embodiments hereof.

Methods of delivering and deploying heart valve prostheses, such as those prostheses described in more detail in U.S. Pat. No. 9,034,032 to McLean et al. and International Patent Application No. PCT/US2014/029549 to McLean et al, each of which is herein incorporated by reference in its entirety, may utilize embodiments of the present invention. Other non-limiting examples of transcatheter heart valve prostheses useful with systems and methods hereof are described in U.S. Patent Application Publication No. 2012/0101572 to Kovalsky et al., U.S. Patent Application Publication No. 2012/0035722 to Tuval, U.S. Patent Application Publication No. 2006/0265056 to Nguyen et al., U.S. Patent Application Publication No. 2007/0239266 to Birdsall, and U.S. Patent Application Publication No. 2007/0239269 to Dolan et al., each of which is incorporated by reference herein in its entirety As shown in FIG. 6, at least the distal tip 602 of the delivery catheter 600 is passed through the catheter receiving opening 202, resulting in the configuration shown in FIG. 7, where the delivery catheter 600, suitably up to at least the distal segment 606, is inserted through the catheter receiving opening 202. The inner component 108 is then proximally translated, such as by sliding motion 210, so as to decrease an area of the catheter receiving opening 202 (e.g., from FIG. 2A showing the catheter receiving opening 202 to FIG. 2B showing a reduced or constricted catheter receiving opening 202'). As shown in FIG. 7, proximally sliding the inner component 108 relative to the outer component 106 holds or secures the delivery catheter 600 between the connecting band 110 and the first outer branch segment 126 and the second outer branch segment 128 of the outer component 106. As described herein, the flexible nature of the connecting band 110 allows it to hold the delivery catheter 600 in place, without damage to the catheter.

Figure 8:
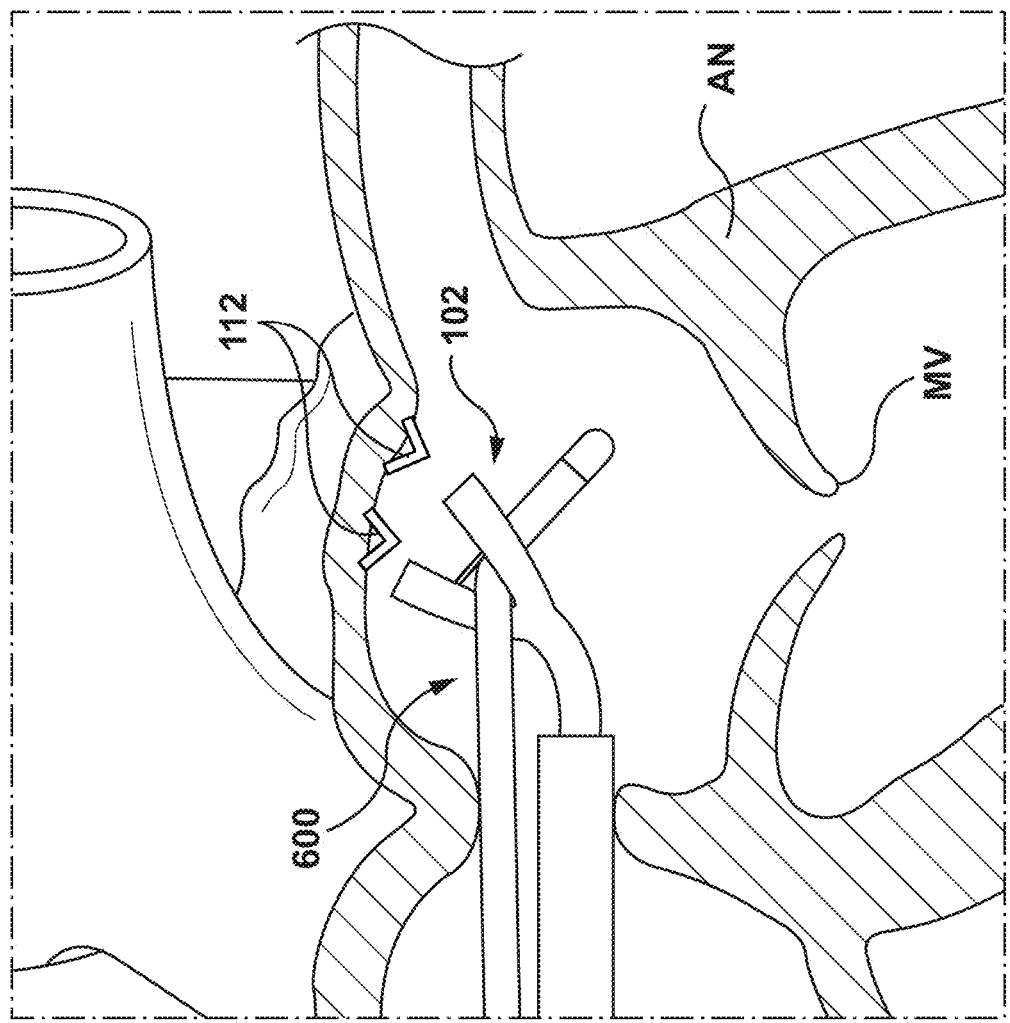
FIG. 8 shows bending of the delivery catheter by manipulating the deflection aid assembly in accordance with embodiments hereof.

The methods described herein may further include bending (or angling) the delivery catheter 600 with the deflection aid assembly 102, so that the distal tip 602 of the delivery catheter 600 is directed toward an annulus (AN) of a mitral valve (MV) (see FIG. 8), or other desired area of the left atrium. In exemplary embodiments, prior to the bending of the delivery catheter 600, the deflection aid assembly 102 may be detached from myocardial tissue of the left atrium of the heart either by detaching attachment mechanisms 112 from the outer component 106, as shown in FIG. 8, or by detaching attachment mechanisms 112 from the myocardial tissue, not shown. While not required, detaching the deflection aid assembly 102 from the myocardial tissue prior to bending the delivery catheter 600 allows more force to be applied to the delivery catheter 600 to facilitate bending and positioning within the left atrium and subsequent positioning within the annulus (AN) of the mitral valve (MV). In other embodiments, by proximally and distally moving the inner component 108 with the connecting band 110 relative to the outer component 106, the delivery catheter 600 can be bent as a result of decreasing the area of the catheter receiving opening 202 to secure the catheter therein and bending the delivery catheter 600 by proximally tugging or pulling on the deflection aid assembly 102. Thereafter, the area of the catheter delivery opening 202 may be increased such that the delivery catheter 600 may be further advanced relative to the deflection aid assembly 102, and then again the inner component 108 and the connecting band 110 may be proximally translated relative to the outer component 106 to tighten around another portion of the delivery catheter 600 and the catheter may be again bent by proximally tugging or pulling on the deflection aid assembly 102. This process may be repeated, as needed, in order to properly position the delivery catheter 600 within the left atrium and/or the mitral valve.

Figure 9:
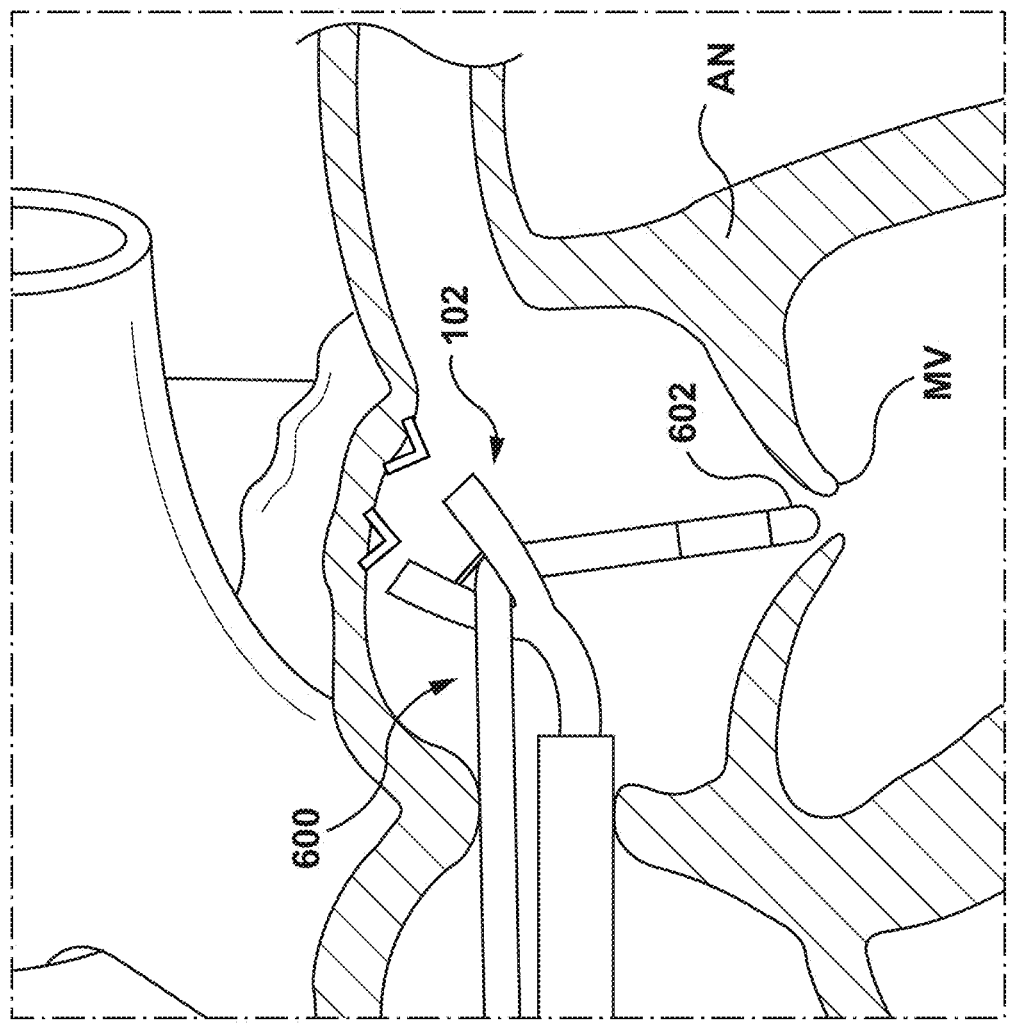
FIG. 9 shows bending and translation of the delivery catheter by manipulating the deflection aid assembly to position a tip of the delivery catheter near a mitral valve in accordance with embodiments hereof.

As shown in FIG. 9, the methods can further comprise bending the delivery catheter 600 with the deflection aid assembly 102 toward the mitral valve (MV), so that the distal tip 602 of delivery catheter 600 passes into or through mitral valve (MV) such that the distal segment 606 may be positioned within the annulus (AN) for deploying a heart valve prosthesis therein. In other embodiments, such manipulation may permit for delivery of a medical device (e.g., heart valve repair devices, leaflet coaptation devices, clips, annuloplasty rings or other annuloplasty mechanisms), into or at the position of the mitral valve (MV).

Figure 10:
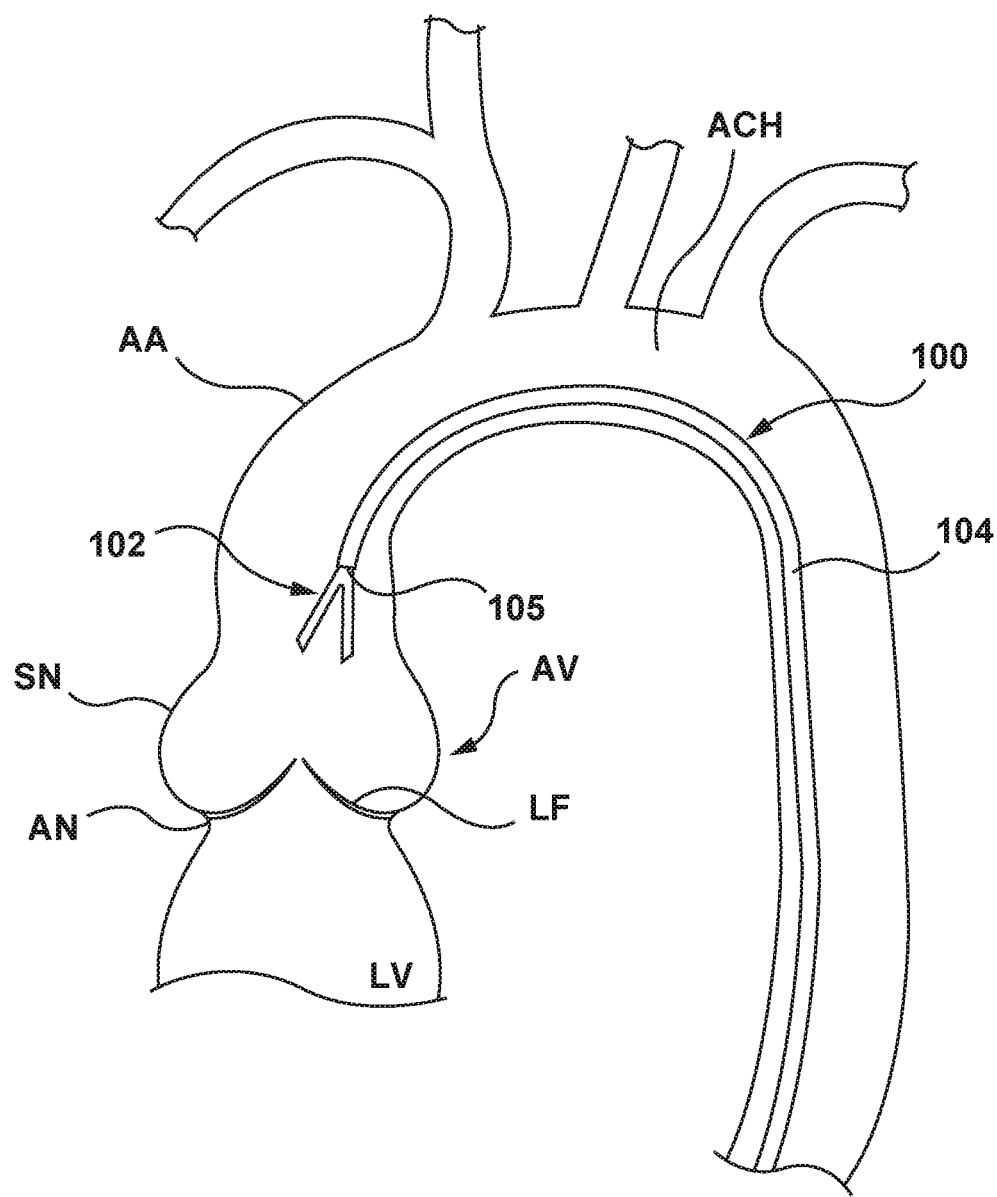
FIG. 10 shows a deflection catheter advanced and position within an ascending aorta adjacent the sinus of an aortic valve.

As also described herein, the deflection catheters are suitably used for positioning a delivery catheter in an aortic valve procedure. With reference to FIG. 10, the deflection catheter 100 is shown after having been introduced into the vasculature via a percutaneous entry point, for example via the Seldinger technique, and tracked through the vasculature into the aorta A, over the aortic arch, and positioned adjacent the sinuses SN of the aortic valve. Prior thereto, intravascular access may be achieved via a percutaneous access site to femoral arterial access up to the common iliac artery and into the aorta, or other known access routes. Thereafter, a guidewire (not shown) may be advanced through the circulatory system to the ascending aorta. Once the guidewire is positioned, the deflection catheter 100 may be advanced (optionally over the guidewire and/or through a guide catheter) to the ascending aorta, adjacent the sinuses SN of the aortic valve AV. Although described with the use of a guide catheter and/or a guidewire, in another embodiment hereof the deflection catheter 100 may access the aorta A without the use of a guidewire and/or a guide catheter. For example, in methods in accordance herewith, the deflection catheter 100 as described herein is suitably advanced up the femoral artery and the aorta A until reaching the right atrium aortic valve AV. Additional methods of introducing the deflection catheter 100 into the aorta are also encompassed herein and are known by those of ordinary skill in the art.

Figure 11:
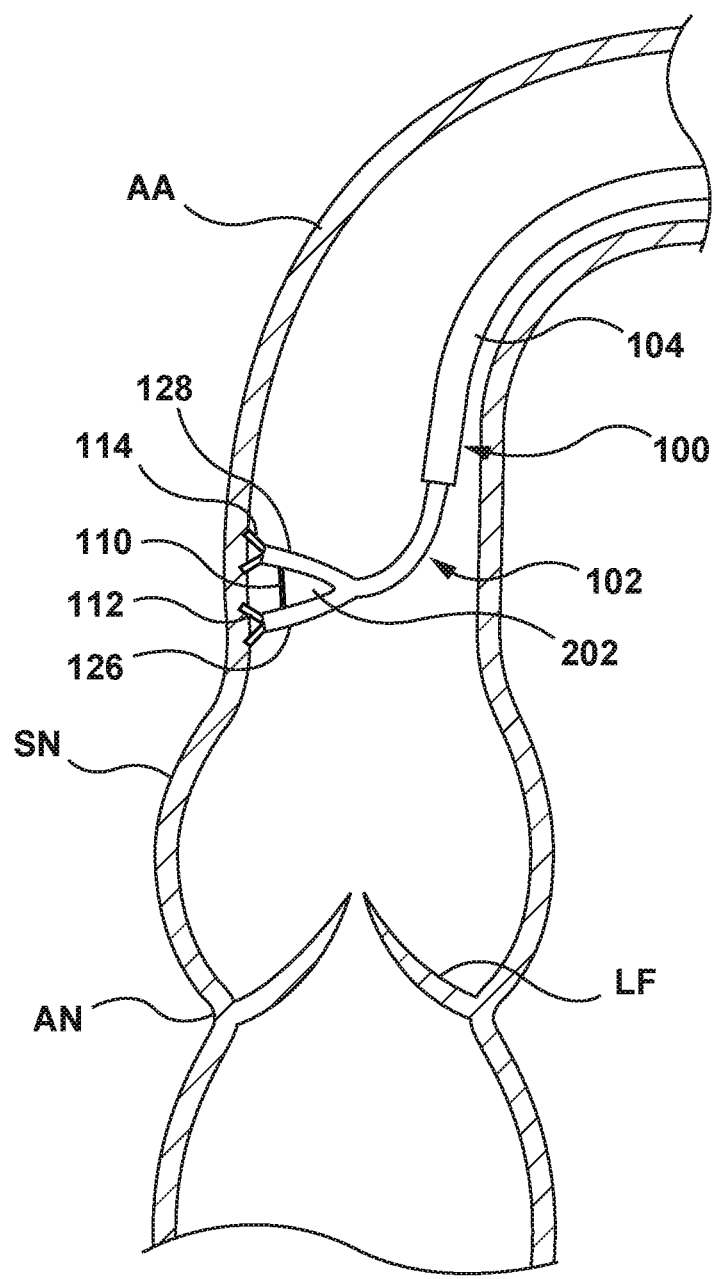
FIG. 11 shows attachment of the deflection aid assembly to a wall of the ascending aorta.

After the deflection catheter 100 is advanced to the ascending aorta AA, the deflection aid assembly 102 is deployed from the distal end 150 of the elongate tubular sheath 104, as shown in FIG. 11. In the deployed configuration, as shown in FIG. 3, the deflection aid assembly 102 may assume a generally Y-shape, as the first outer branch segment 126 and the second outer branch segment 128 of the outer component 106, with the first inner branch segment 132 and the second inner branch segment 134 of the inner component 108 disposed respectively therein, diverge from each other. As well upon deployment of the deflection aid assembly 102 from the distal end 150 of the elongate tubular sheath 104, the proximal segments 124, 130 of the outer and inner components 106, 108 may assume a curved configuration. When the deflection aid assembly 102 is in the deployed configuration, as shown in FIGS. 11 and 12, the catheter receiving opening 202 is open and accessible, and the curved configuration permits for attaching of attachment mechanisms 112 to the wall of the ascending aorta AA, as shown in FIG. 11.

Figure 12:
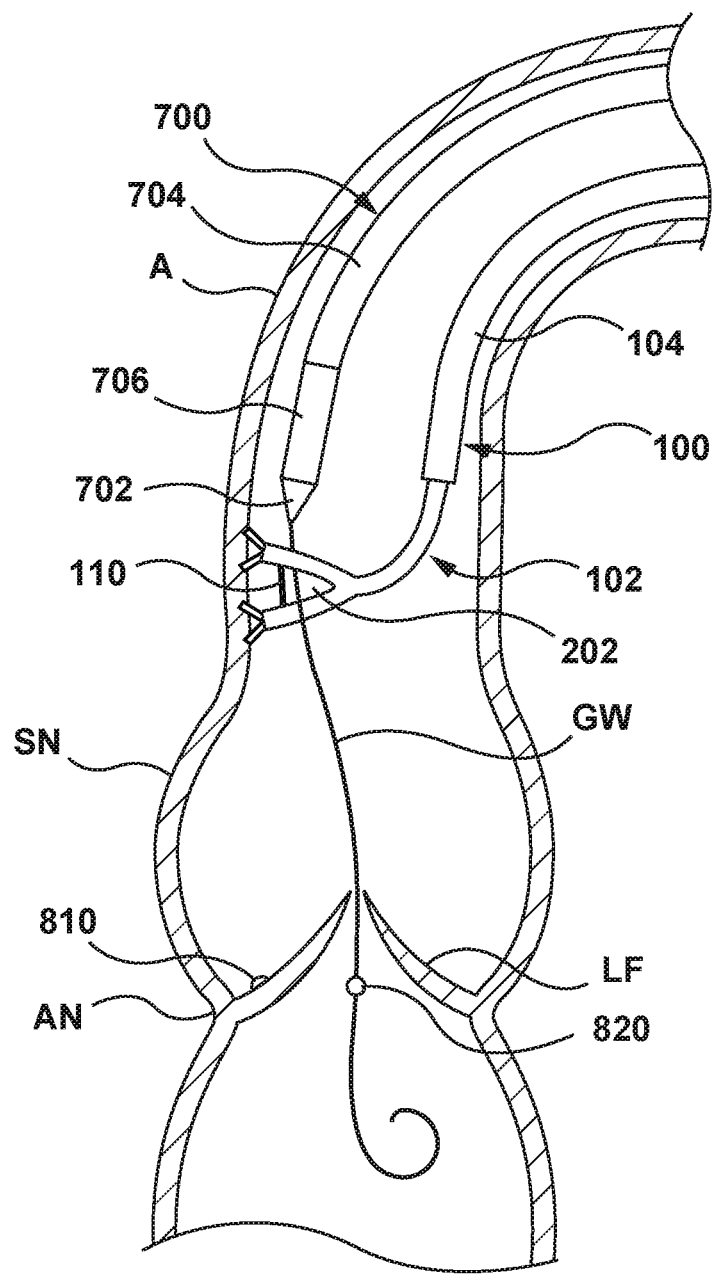
FIG. 12 shows advancement of a delivery catheter through the aorta and into a catheter receiving opening of the deflection aid assembly in accordance with embodiments hereof.

The methods provided herein further include introducing a delivery catheter 700 into the ascending aorta, as shown in FIG. 12. As described above, when a delivery catheter, such as the delivery catheter 700 for delivering, for example, a transcatheter prosthetic valve, is advanced over the aortic arch ACH, the delivery catheter tends to track on the outside curvature of the aorta, as shown in FIG. 12. In such a situation, a distal nosecone or tip 702 of the delivery catheter 700 lines up with an axis extending to a location 810 where the native valve leaflets LF attach to the annulus AN. However, it is preferable that the delivery catheter 700 align along a central axis 820 of the annulus AN. As with delivery catheter 600 described briefly above, delivery catheter 700 may include an elongate tubular sheath 704, which may include a distal segment 706, such as a capsule segment, within which a medical device, such as a prosthetic heart valve (not shown), may be held in a delivery state, as shown in FIG. 11. The delivery catheter 700 may assume different forms, construction and features described, by example and not by way of limitation, in U.S. Pat. No. 8,876,893 to Dwork, U.S. Pat. No. 7,662,186 to Bragga et al., U.S. Pat. No. 7,740,655 to Birdsall, and/or U.S. Pat. No. 8,579,963 to Tabor, each of which is incorporated by reference herein in their entirety. Delivery catheters, also known as medical catheters, are typically adapted to deliver and deploy medical devices, such as prosthetic heart valves, stent-grafts, and stents to selected targeted sites in the body. Delivery catheters may also be utilized with a guidewire. Medical devices typically are releasably carried within a distal region of the delivery catheter in a radially compressed delivery state as the catheter is navigated to and positioned at a target treatment/deployment site.

Methods of delivering and deploying heart valve prostheses, such as a prosthetic valve a prosthetic valve sold under the trade name CoreValve® available from Medtronic CoreValve, LLC., and prosthetic valves described in more detail in U.S. Pat. No. 9,504,564 to Nguyen et al., U.S. Pat. No. 7,740,655 to Birdsall, and U.S. Patent Application Publication No. 2007/05409269 to Dolan et al., each of which is herein incorporated by reference in its entirety, may utilize embodiments of the present invention.

Figure 13:
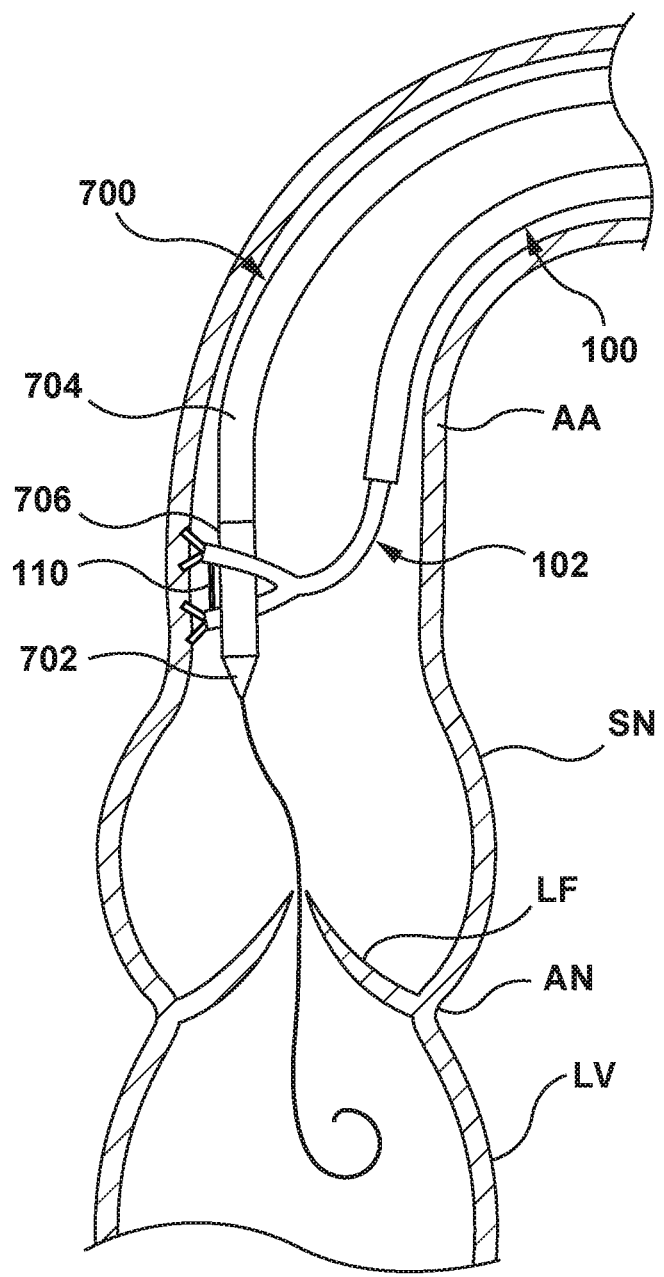
FIG. 13 shows securing of the delivery catheter by the deflection aid assembly in accordance with embodiments hereof.
Figure 14:
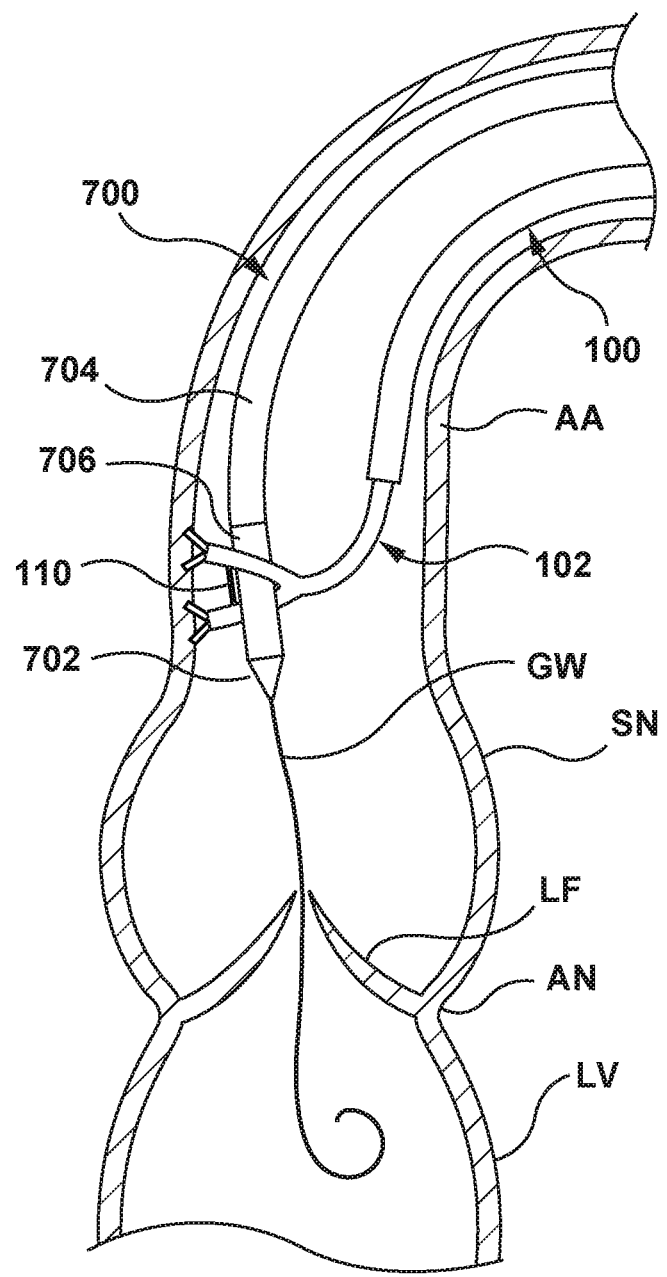
FIG. 14 shows bending of the delivery catheter by manipulating the deflection aid assembly in accordance with embodiments hereof.

At least the distal tip 702 of the delivery catheter 700 is passed through the catheter receiving opening 202, resulting in the configuration shown in FIG. 13, where the delivery catheter 700, suitably up to at least the distal segment 706, is disposed through the catheter receiving opening 202. The inner component 108 (not shown in FIG. 14) is then proximally translated, such as by a sliding motion, thereby moving connecting band 110 towards the fork in the outer member 106 so as to decrease an area of the catheter receiving opening 202 (e.g., from FIG. 2A showing the catheter receiving opening 202 to FIG. 2B showing a reduced or constricted catheter receiving opening 202'). As shown in FIGS. 13-14, proximally sliding the inner component 108 relative to the outer component 106 holds or secures the delivery catheter 700 between the connecting band 110 and the first outer branch segment 126 and the second outer branch segment 128 of the outer component 106. As described herein, the flexible nature of the connecting band 110 allows it to hold the delivery catheter 700 in place, without damage to the catheter. In some embodiments of the deflection catheter 100 and the delivery catheter 700, moving the inner component 108 of the deflection aid assembly 102 relative to the outer component 106 such that the connecting band 110 moves the catheter 700 towards the fork and holds the catheter the delivery catheter 700 between the connecting band 110, the first outer branch segment 126, and the second outer branch segment 128, may be sufficient to move the delivery catheter 700 such that it aligns with the central axis 810 of the annulus AN, as shown in FIG. 14.

Figure 15:
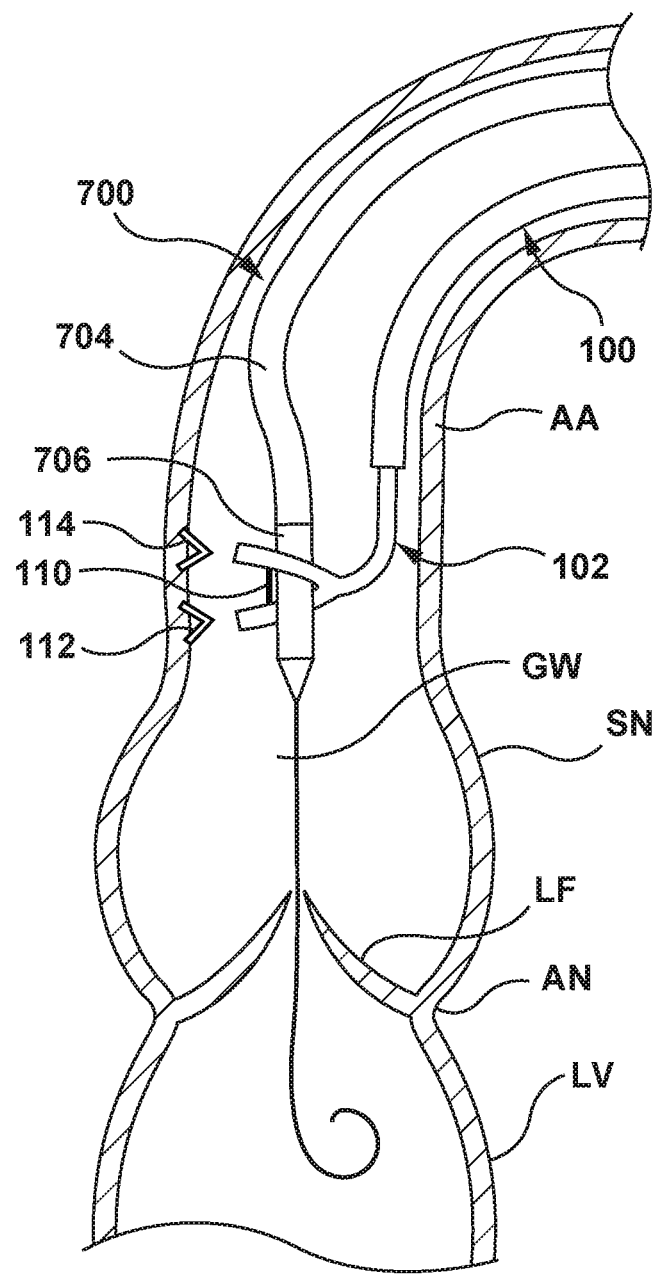
FIG. 15 shows further bending of the delivery catheter by manipulating the deflection aid assembly in accordance with other embodiments hereof.

In other embodiments, the methods described herein may include further bending (or angling) the delivery catheter 700 with the deflection aid assembly 102, so that the distal tip 702 of the delivery catheter 700 is directed toward the central axis 810 of the annulus AN of the aortic valve AV. In exemplary embodiments, prior to the bending of the delivery catheter 700, the deflection aid assembly 102 may be detached from wall of the ascending aorta AA either by detaching attachment mechanisms 112 from the outer component 106, as shown in FIG. 15, or by detaching attachment mechanisms 112 from the wall of the ascending aorta, not shown. While not required, detaching the deflection aid assembly 102 from the wall of the ascending aorta prior to bending the delivery catheter 700 allows more force to be applied to the delivery catheter 700 to facilitate bending and positioning the delivery catheter 700 for accurate delivery to the annulus AN of the aortic valve AV. As noted above, in other embodiments, by proximally and distally moving the inner component 108 with the connecting band 110 relative to the outer component 106, the delivery catheter 700 can be bent as a result of decreasing the area of the catheter receiving opening 202 to secure the catheter therein and bending the delivery catheter 700 by proximally tugging or pulling on the deflection aid assembly 102. Thereafter, the area of the catheter delivery opening 202 may be increased such that the delivery catheter 600 may be further advanced relative to the deflection aid assembly 102, and then again the inner component 108 and the connecting band 110 may be proximally translated relative to the outer component 106 to tighten around another portion of the delivery catheter 600 and the catheter may be again bent by proximally tugging or pulling on the deflection aid assembly 102. This process may be repeated, as needed, in order to properly position the delivery catheter 600 within the left atrium and/or the mitral valve.

Figure 16:
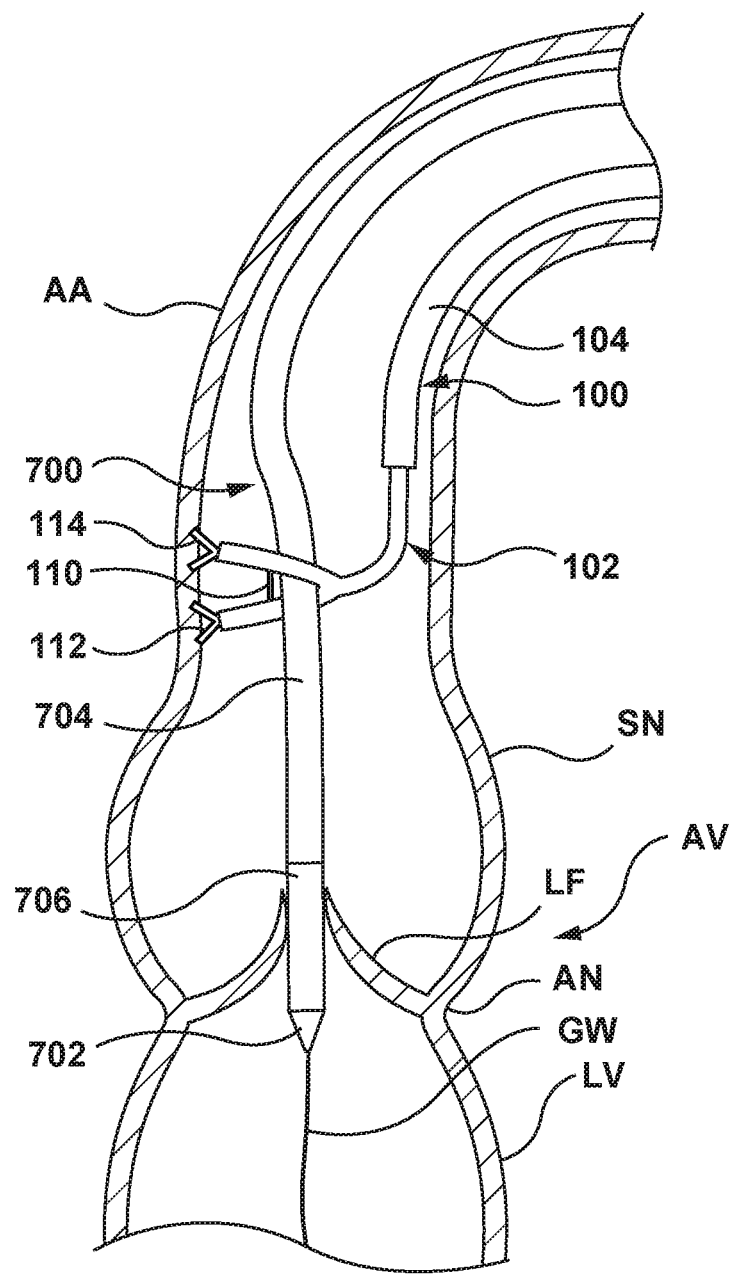
FIG. 16 shows bending and translation of the delivery catheter through the deflection aid assembly to position a tip of the delivery catheter at the annulus of the native aortic valve in accordance with embodiments hereof.

As shown in FIG. 16, the methods can further comprise advancing the delivery catheter 700 along the central axis 810 of the annulus AN through the native valve leaflets LF such that at least part of the distal segment 706 of the delivery catheter 700 is aligned with the annulus AN. Further steps for deploying the prosthetic valve from the delivery catheter 700, known to those skilled in the art, may then be performed. Further, in other embodiments, such manipulation and advancement may permit for delivery of a medical device (e.g., heart valve repair devices, leaflet coaptation devices, clips, annuloplasty rings or other annuloplasty mechanisms), into or at the position of the aortic valve AV. FIG. 16 shows that delivery catheter 700 advanced with the deflection aid assembly 102 attached to the wall of the ascending aorta AA. As explained above, in other embodiments, the deflection aid assembly 102 may first be detached from the wall of the ascending aorta AA, While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A deflection catheter comprising:
   a deflection aid assembly including,
   an outer component having a proximal segment, a first outer branch segment, and a second outer branch segment,
   an inner component having a proximal segment slideably disposed within the proximal segment of the outer component, and having a first inner branch segment and a second inner branch segment slideably disposed with the first outer branch segment and the second outer branch segment, respectively, of the outer component,
   a connecting band connecting the first inner branch segment and the second inner branch segment of the inner component, the connecting band extending between the first outer branch segment and the second outer branch segment of the outer component such that a catheter receiving opening is defined between the connecting band and the first outer branch segment and the second outer branch segment, wherein proximal and distal movement of the inner component relative to the outer component increases or decreases an area of the catheter receiving opening, and
   an attachment mechanism coupled to a distal portion of at least one of the first outer branch segment or the second outer branch segment of the outer component, the attachment mechanism being configured to attach the at least one of the first outer branch segment or the second outer branch segment to tissue of a wall of a heart or a vessel within a patient.

2. The deflection catheter of claim 1, wherein each of the first outer branch segment and the second outer branch segment of the outer component has a slotted opening through which the connecting band passes so as to connect the first inner branch segment and the second inner branch segment disposed, respectively, therein.

3. The deflection catheter of claim 1, wherein the attachment mechanism is detachable from the first outer branch segment and/or the second outer branch segment.

4. The deflection catheter of claim 1, wherein the first outer branch segment and the second outer branch segment comprise a low friction coating adjacent the catheter receiving area.

5. The deflection catheter of claim 1, wherein the first outer branch segment and the second outer branch segment distally extend from the proximal segment of the outer component such that the outer component has a generally Y-shape.

6. The deflection catheter of claim 5, wherein the first inner branch segment and the second inner branch segment distally extend from the proximal segment of the inner component such that the inner component has a generally Y-shape that is substantially similar to the generally Y-shape of the outer component.

7. The deflection catheter of claim 1, further comprising:
   an elongate tubular sheath defining a lumen within which the deflection aid assembly is slideably disposed.

8. The deflection catheter of claim 7, wherein when the deflection aid assembly is in a delivery configuration within the lumen of the elongate tubular sheath, the first outer branch segment and the second outer branch segment of the outer component, with the first inner branch segment and the second inner branch segment of the inner component disposed respectively therein, are held in a low-profile state.

9. The deflection catheter of claim 8, wherein when the deflection aid assembly is translated to be free of a distal end of the elongate tubular sheath and assumes a deployed configuration, the first outer branch segment and the second outer branch segment, with the first inner branch segment and the second inner branch segment of the inner component disposed respectively therein, diverge from each other to a deployed state.

10. The deflection catheter of claim 9, wherein upon deployment of the deflection aid assembly from the distal end of the elongate tubular sheath, the proximal segments of the inner and outer components assume a curved configuration.

11. A method of bending a catheter or other elongate medical device comprising:
percutaneously advancing a deflection catheter to a desired location, the deflection catheter including an elongate tubular sheath defining a lumen and a deflection aid assembly slideably disposed within the lumen, the deflection aid assembly including,
an outer component having a proximal segment, a first outer branch segment, and
a second outer branch segment,
an inner component having a proximal segment slideably disposed within the proximal segment of the outer component, and having a first inner branch segment and a second inner branch segment slideably disposed with the first outer branch segment and the second outer branch segment, respectively, of the outer component,
a connecting band connecting the first inner branch segment and the second inner branch segment of the inner component, the connecting band extending between the first outer branch segment and the second outer branch segment of the outer component such that a catheter receiving opening is defined between the connecting band and the first outer branch segment and the second outer branch segment, wherein proximal and distal movement of the inner component relative to the outer component increases or decreases an area of the catheter receiving opening, and
an attachment mechanism associated with at least one of the first outer branch segment or the second outer branch segment of the outer component;
deploying the deflection aid assembly from the distal end of the elongate tubular sheath of the deflection catheter whereby the first outer branch segment and the second outer branch segment of the outer component, with the first inner branch segment and the second inner branch segment of the inner component disposed respectively therein, diverge from each other;
attaching the attachment mechanism of the deflection aid assembly to a wall at the desired location;
advancing a catheter or other elongate medical device to the desired location;
advancing at least a distal tip of the catheter or other elongate medical device through the catheter receiving opening of the deflection aid assembly of the deflection catheter;
proximally sliding the inner component of the deflection aid assembly relative to the outer component of the deflection aid assembly so as to decrease the area of the catheter receiving opening and thereby to secure the catheter or other elongate medical device between the connecting band and the first outer branch segment and the second outer branch segment of the outer component.

12. The method of claim 11, further comprising bending the catheter or other elongate medical device by proximally tugging or pulling on the deflection aid assembly of the deflection catheter.

13. The method of claim 12, wherein the step of bending includes bending the catheter or other elongate medical device with the deflection aid assembly so that the distal tip of the catheter or other elongate medical device is directed in a desired direction.

14. The method of claim 12, further comprising detaching the deflection aid assembly from the subject's heart prior to the bending.

15. The method of claim 12, wherein the bending comprises bending the delivery catheter toward the mitral valve so that the tip of the delivery catheter passes into or through an annulus of the mitral valve.

16. The method of claim 12,
wherein the desired location is an aortic valve,
wherein the wall to which the deflection aid assembly is attached is a wall of an ascending aorta.

17. The method of claim 16, wherein the step of bending includes bending the catheter or other elongate medical device with the deflection aid assembly such that the distal tip of the catheter or other elongate medical device is directed toward an annulus of the aortic valve along a central axis of the annulus.

18. The method of claim 12,
wherein the desired location is a left atrium of a heart,
wherein the wall to which the deflection aid assembly is attached is a wall of the left atrium.

19. The method of claim 17, wherein the step of bending includes bending the catheter or other elongate medical device with the deflection aid assembly such that the distal tip of the catheter or other elongate medical device is directed toward an annulus of the mitral valve.

* * * * *